United States Patent (10) Patent No.: US 11,238,580 B2
Laaksonen et al. (45) Date of Patent: Feb. 1, 2022

(54) SYSTEMS AND METHODS FOR IMAGE CROPPING AND ANATOMICAL STRUCTURE SEGMENTATION IN MEDICAL IMAGING

(71) Applicant: VARIAN MEDICAL SYSTEMS INTERNATIONAL AG, Steinhausen (CH)

(72) Inventors: Hannu Laaksonen, Espoo (FI); Janne Nord, Espoo (FI); Jan Schreier, Helsinki (FI)

(73) Assignee: VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 138 days.

(21) Appl. No.: 16/554,742

(22) Filed: Aug. 29, 2019

(65) Prior Publication Data
US 2021/0065360 A1 Mar. 4, 2021

(51) Int. Cl.
*G06T 7/11* (2017.01)
*G06T 7/00* (2017.01)
(Continued)

(52) U.S. Cl.
CPC ............. *G06T 7/0012* (2013.01); *G06N 3/08* (2013.01); *G06T 7/11* (2017.01); *A61N 5/1047* (2013.01);
(Continued)

(58) Field of Classification Search
CPC ..... G06T 7/00; G06T 3/00; G06T 7/11; G06T 7/70; G06T 7/149; G06T 7/38; G06T 7/174; G06T 7/73; G06T 7/90; G06T 11/00; G06T 2207/10016; G06T 2207/10024; G06T 2207/20081; G06T 2207/30201; G06T 2207/30241; G06T 2207/30244;
(Continued)

(56) References Cited

U.S. PATENT DOCUMENTS 9,633,306 B2 4/2017 Liu et al.
10,062,014 B2 8/2018 Zhou et al.
(Continued)

OTHER PUBLICATIONS

Zarpalas et al., "Accurate and Fully Automatic Hippocampus Segmentation Using Subject-Specific 3D Optimal Local Maps Into a Hybrid Active Contour Model," Medical Imaging and Diagnostic Radiology, IEEE Journal of Translational Engineering in Health and Medicine, vol. 2, 2014.
(Continued)

*Primary Examiner* — Quan M Hua
(74) *Attorney, Agent, or Firm* — SGPatents PLLC

(57) ABSTRACT

One or more medical images of a patient are processed by a first neural network model to determine a region-of-interest (ROI) or a cut-off plane. Information from the first neural network model is used to crop the medical images, which serves as input to a second neural network model. The second neural network model processes the cropped medical images to determine contours of anatomical structures in the medical images of the patient. Each of the first and second neural network models are deep neural network models. By use of cropped images in the training and inference phases of the second neural network model, contours are produced with sharp edges or flat surfaces.

35 Claims, 7 Drawing Sheets

(51) Int. Cl.
*G06N 3/08* (2006.01)
*G06T 7/174* (2017.01)
*A61N 5/10* (2006.01)

(52) U.S. Cl.
CPC .... *G06T 7/174* (2017.01); *G06T 2207/10072* (2013.01); *G06T 2207/20081* (2013.01); *G06T 2207/20084* (2013.01); *G06T 2207/20221* (2013.01); *G06T 2207/30096* (2013.01)

(58) Field of Classification Search
CPC .. G06T 7/251; G06T 7/74; G06T 7/80; A61B 5/00; A61B 5/055; A61B 5/01; A61B 5/11; A61B 5/15; A61B 5/16; G16H 30/40; G16H 10/60; G16H 50/20; G16H 40/63; G06N 3/08; G06N 3/04; G06N 5/04; G06N 3/0454; G06N 3/084; G06K 9/00; G06K 9/46; G06K 9/00261; G06K 9/00288; G06K 9/00228; G06K 9/00268; G06K 9/00281; G06K 9/6202; G06K 2009/4666; G06K 9/00362; G06K 9/4642; G06K 9/6206; G06K 9/6255; G06K 9/6256; G06K 9/00275; G06K 9/00308; G06K 9/00926; G06K 9/3233; G06K 9/4671; G06K 9/6215; G06K 9/6228; G06K 9/6262; G06K 9/627; G06K 9/6276; G06K 9/629
See application file for complete search history.

(56) References Cited

U.S. PATENT DOCUMENTS

| | | | |
|---|---|---|---|
| 10,127,659 B2 | 11/2018 | Hsieh et al. | |
| 10,223,788 B2 | 3/2019 | Bozorgtabar et al. | |
| 10,346,986 B2 | 7/2019 | Xu et al. | |
| 2015/0317790 A1* | 11/2015 | Choi | G06T 7/0012 382/128 |
| 2017/0109881 A1* | 4/2017 | Avendi | G06T 7/149 |
| 2019/0030371 A1* | 1/2019 | Han | G16H 50/20 |

OTHER PUBLICATIONS

Andrey et al., "Adaptive Active Contours (Snakes) for the Segmentation of Complex Structures in Biological Images." Internet download Aug. 2019.
Kashani et al., "Practical Workflow and the Cost of Adaptive Therapy," Washington University School of Medicine, Mar. 7, 2015.
Jahromi et al., "An Automatic Algorithm for Segmentation of the Boundaries of Corneal Layers in Optical Coherence Tomography Images Using Gaussian Mixture Model," Journal of Medical Signals & Sensors, vol. 4, Issue 3, July-Sep. 2014, pp. 171-180.
Deniz et al., "Segmentation of the Proximal Femur from MR Images using Deep Convolutional Neural Networks," Scientific Reports, (2018) 8:16485 | DOI:10.1038/s41598-018-34817-6.
Li et al., "Automatic Segmentation of Liver Tumor in CT Images with Deep Convolutional Neural Networks," Journal of Computer and Communications, 2015, 3, pp. 146-151.
Sadeghi-Tehran et al., "Multi-Feature Machine Learning Model for Automatic Segmentation of Green Fractional Vegetation Cover for High-Throughput Field Phenotyping," Plant Methods (2017) 13:103 DOI 10.1186/s13007-017-0253-8.
Codella et al., "Automatic Left Ventricle Segmentation Using Interactive Thresholding and Active Contour Model With Adaptation on Short-Axis Cardiac MRI," Article in IEEE transactions on bio-medical engineering, Mar. 2009, DOI: 10.1109/TBME.2009.2014545, PubMed.
Schaefer et al., "Manifold Dual Contouring," Texas A&M University, College Station, TX, Washington University, St. Louis, MO, Rice University, Houston, TX., Internet download Aug. 2019.
Feng et al., "Deep Convolutional Neural Network for Segmentation of Thoracic Organs-at-risk Using Cropped 3D Images," Med. Phys. 46 (5), May 2019, pp. 2169-2180.
Parthasarathy, "A Brief History of CNNs in Image Segmentation: From R-CNN to Mask R-CNN", Apr. 22, 2017.
Lundervold et al., "An Overview of Deep Learning in Medical Imaging Focusing on MRI," Z Med. Phys., 29 (2019), pp. 102-127.
Ramkumar et al., "User Interface Concept and New Workflow," Delft University of Technology, 2014.
International Search Report and Written Opinion dated Oct. 30, 2020, in International Patent Application No. PCT/EP2020/073769.

* cited by examiner

US 11,238,580 B2

SYSTEMS AND METHODS FOR IMAGE CROPPING AND ANATOMICAL STRUCTURE SEGMENTATION IN MEDICAL IMAGING

FIELD

The present disclosure relates generally to medical imaging, and more particularly, to systems and methods for image cropping and anatomical structure segmentation in medical images, such as images used for radiotherapy treatment planning.

BACKGROUND

Radiotherapy is an important tool for the treatment of cancerous tumors in patients. Unfortunately, ionizing radiation applied to treat the patient does not inherently discriminate between tumors and proximal healthy structures (e.g., organs-at-risk). Administration of the ionizing radiation thus must be carefully tailored to restrict the applied radiation to the target (i.e., tumor) while avoiding unnecessary irradiation of surrounding anatomy, the goal being to deliver a lethal radiation dose to the tumor while maintaining an acceptable dosage to the proximal structures.

As part of the radiotherapy planning process, medical images of the tumor and surrounding anatomy are obtained. The medical images can serve as a basis for simulations of the radiation treatment and can be used to plan various aspects of the therapy, including but not limited to, beam geometry and location, radiation energy, and dosage. The medical images are typically processed to delineate target regions (e.g., pixels or voxels where a tumor or other regions desired to be irradiated are imaged) and separate surrounding structures (e.g., pixels or voxels where an organ-at-risk (OAR) or other anatomical structure to avoid being irradiated is imaged). This delineation, termed contouring or segmenting, involves defining a respective border defining outlines of the different anatomical structures in the image. However, if anatomical structures are improperly contoured in the images, this could result in insufficient irradiation of the target and/or undesirable irradiation of surrounding structures.

Manual contouring of structures in medical images can be a time-consuming phase in the radiotherapy planning process. To address this issue, automatic segmentation models have been proposed. However, existing methodologies suffer from inaccuracies at the border of structures. For example, there may be limited anatomical information at a border to stop contouring. In some cases, the ground truth may be inconsistent on the exact border, but the border itself would necessarily be a straight cut (i.e., on a flat plane) due to clinical practices. In such situations, existing automatic segmentation methodologies would apply a round or smooth transition to the generated contour, as it seeks to find a balance between contours in the training data. Since the training data may not agree on where the cut-off should be, existing methodologies cannot easily be trained to have sharp cut-offs. Moreover, users (e.g., radiologist or radiation therapist) might have their own preferences on how to contour structures, which preferences may differ from baseline segmentation guidelines. Employing existing methodologies thus requires the user to correct part of the resulting contour by hand, which can be time-consuming.

One example of such a scenario is in defining the superior border of the breast. For example, FIG. 1A shows an exemplary two-dimensional image 100 of breast 102 with a contour 104 generated by an automatic segmentation method. Although there is no clear anatomical landmark, clinicians may prefer an axial cut 108 at the superior end 106 of the breast 102. However, existing segmentation methodologies may result in a rounded contour 104s at the superior end 106. A user may thus need to correct the generated contour 104 to have the desired straight cut 108.

In some scenarios, an organ or structure may only be partially delineated. For example, the user may prefer to segment the spine only in a region of expected radiation (e.g., based on radiation field information), instead of everywhere in the image where the spine is present. In order to save time and processing resources, the user may define a bounding box 110 with flat edges that define the portions of spine 122 in image 120 that should be contoured, as illustrated in FIG. 1B. Again, however, existing segmentation methodologies may result in rounded contours for the spine 122 at the top 124 and bottom 126 edges of bounding box 110, rather than straight edges as the sharp cut-off defined by bounding box 110 would otherwise dictate. The user may thus need to correct the contours generated by existing segmentation methodologies.

In some scenarios, a range of computed tomography (CT) image slices are used to form a three-dimensional (3-D) image of anatomical structures. However, since the range of slices may be insufficient to image the entire anatomical structure, a sharp cut-off in a two-dimensional plane can result with respect to some anatomical structures. For example, FIG. 1C illustrates a CT image stack 130 of anatomical structure 132, where 134 represent exemplary axial slices that are assembled to form a 3-D image. Corresponding 2-D image slices in the sagittal direction 138 or coronal direction 136 can also be formed from the 3-D image. Note that only a portion of the slices in each direction have been illustrated in the figure for clarity. Since the structure 132 extends beyond the stack 130 of images in the axial direction, sagittal slices 138 and coronal slices 136 have sharp cuts for anatomical structure 132 defined by top 2-D plane 140 and bottom 2-D plane 142. Existing segmentation methodologies may result in rounded contours for the spine structure at the top 140 and bottom 142 planes in such slices 136, 138, thereby requiring intervention by the user to correct.

Embodiments of the disclosed subject matter may address one or more of the above-noted problems and disadvantages, among other things.

SUMMARY

Embodiments of the disclosed subject matter provide first and second neural network models for processing medical images of a patient to produce improved contours of anatomical structures. One or more medical images of a patient can be processed by one or more first neural network models to determine regions-of-interest (ROIs) or cut-off planes. Information from the one or more first neural network models is used to crop the medical images, which serves as input to one or more second neural network models. The one or more second neural network models can process the cropped medical images to determine contours of anatomical structures in the medical images of the patient. Each of the first and second neural network models is a deep neural network model, having at least two hidden layers of nodes between input and output layers. For example, contours may be produced with sharp edges or flat surfaces by use of images cropped according to the first neural network model in the training and inference phases of the second neural network model.

In one or more embodiments, a method comprises training at least one first neural network model using a first data set of medical images. Each of the medical images in the first data set can include a contour of an anatomical structure therein and at least one of a region-of-interest (ROI) around the anatomical structure and a cut-off plane with respect to the anatomical structure. Each first neural network model can be trained to approximate the ROI or the cut-off plane. The method can further comprise, based on data from the at least one first neural network model, cropping medical images of a second data set. Each of the medical images in the second data set can include a contour of the anatomical structure. The method can also comprise training at least one second neural network model using the cropped medical images, each second model being trained to approximate the contour of the anatomical structure.

In one or more embodiments, a method comprises processing a data set of medical images of a patient using at least one first neural network model to generate cropping data, and cropping the data set of medical images based at least on the cropping data from the at least one first neural network model. The method can also comprise processing the cropped third data set of medical images using at least one second neural network model to generate one or more contours of anatomical structures in the data set of medical images.

In one or more embodiments, a system comprises one or more data storage devices and one or more processors operatively coupled to the one or more data storage devices. The one or more data storage devices can store at least one first neural network model and at least one second neural network model. Each first neural network model can be trained to approximate a region-of-interest (ROI) around an anatomical structure or a cut-off plane with respect to the anatomical structure. Each second neural network model can be trained to approximate a contour of the anatomical structure. The one or more processors can be configured to employ the at least one first neural network model to process one or more medical images of a patient to generate cropping data and to crop the one or more medical images of the patient based at least one the cropping data from the at least one first neural network model. The one or more processors can also be configured to employ the at least one second neural network model to process the one or more cropped medical images of the patient to generate one or more contours of anatomical structures in the medical images of the patient.

In one or more embodiments, a non-transitory computer-readable storage medium and a computer processing system can be provided. The non-transitory computer-readable storage medium can have embodied thereon a sequence of programmed instructions. The computer processing system can be configured to execute the sequence of programmed instructions embodied on the computer-readable storage medium to cause the computer processing system to process one or more medical images of a patient using at least one first neural network model to generate cropping data, to crop the one or more medical images of the patient based at least on the cropping data from the at least one first neural network model, and to process the one or more cropped medical images of the patient using at least one second neural network model to generate one or more contours of anatomical structures in the one or more medical images of the patient. Each first neural network model can be trained to approximate a region-of-interest (ROI) around an anatomical structure or a cut-off plane with respect to the anatomical structure. Each second neural network model can be trained to approximate contours of anatomical structures.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

In various embodiments of the disclosed subject matter, medical images of a patient are processed by at least two neural network models. The first neural network model is used to find the correct cut-off planes or region-of-interest (ROI) in the medical images for one or more anatomical structures (e.g., target or organ-at-risk (OAR)). The data from the first neural network model is then used to crop the medical images to select a tight ROI, and these cropped images are used as input to the second neural network model. The second neural network model processes the cropped images to automatically define contours of the anatomical structures within the medical images. Since the second neural network model has been trained on cropped images from the first neural network model, the second neural network model learns that the cut is always straight at the border of the ROI, and the contour output would not suffer from rounded edges.

Each of the first and second neural network models can be implemented as separate deep neural network (DNN) models. As used herein, the terms "deep learning model" or "deep neural network model" refer to a class of computer-based machine-learning algorithms that utilize many layers or stages (in particular, at least two "hidden" layers between input and output layers) of data processing for feature learning, pattern analysis, and/or classification. In general, these DNN models are formed by a layered network of processing elements (referred to as neurons or nodes) that are interconnected by connections (referred to as synapses or weights). The layers of nodes are trained from end-to-end (i.e., from input layer to output layer) to extract feature(s) from the input and classify the feature(s) to produce an output (e.g., classification label or class).

Figure 1A:
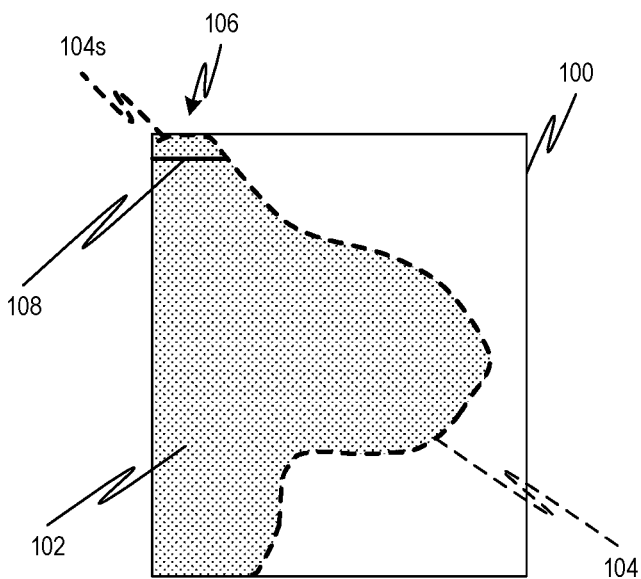
FIGS. 1A-1B are two-dimensional image slices of anatomical structures to illustrate certain issues with conventional segmentation methodologies.
Figure 1B:
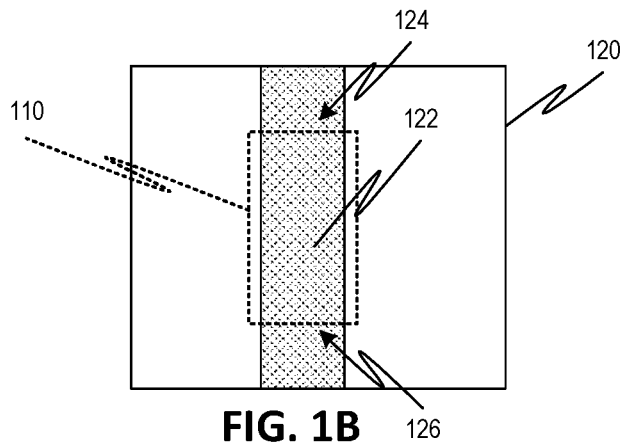
Figure 1C:
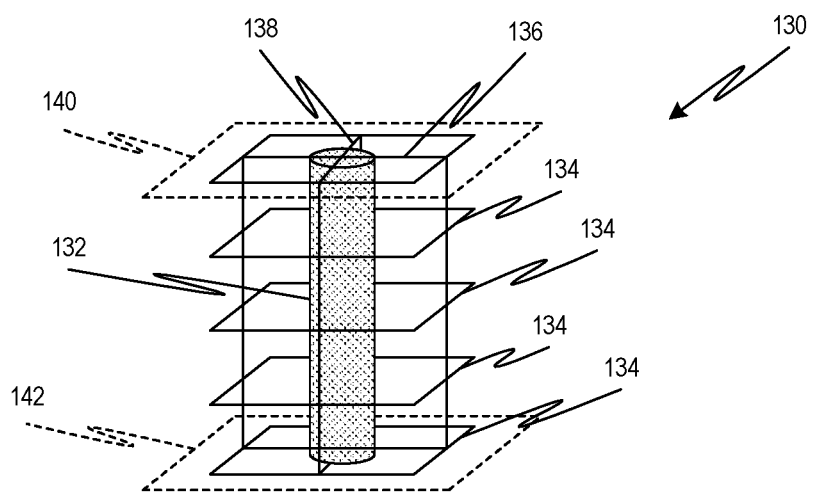
FIG. 1C is a three-dimensional image stack of an anatomical structure to illustrate certain issues with conventional segmentation methodologies.
Figure 2A:
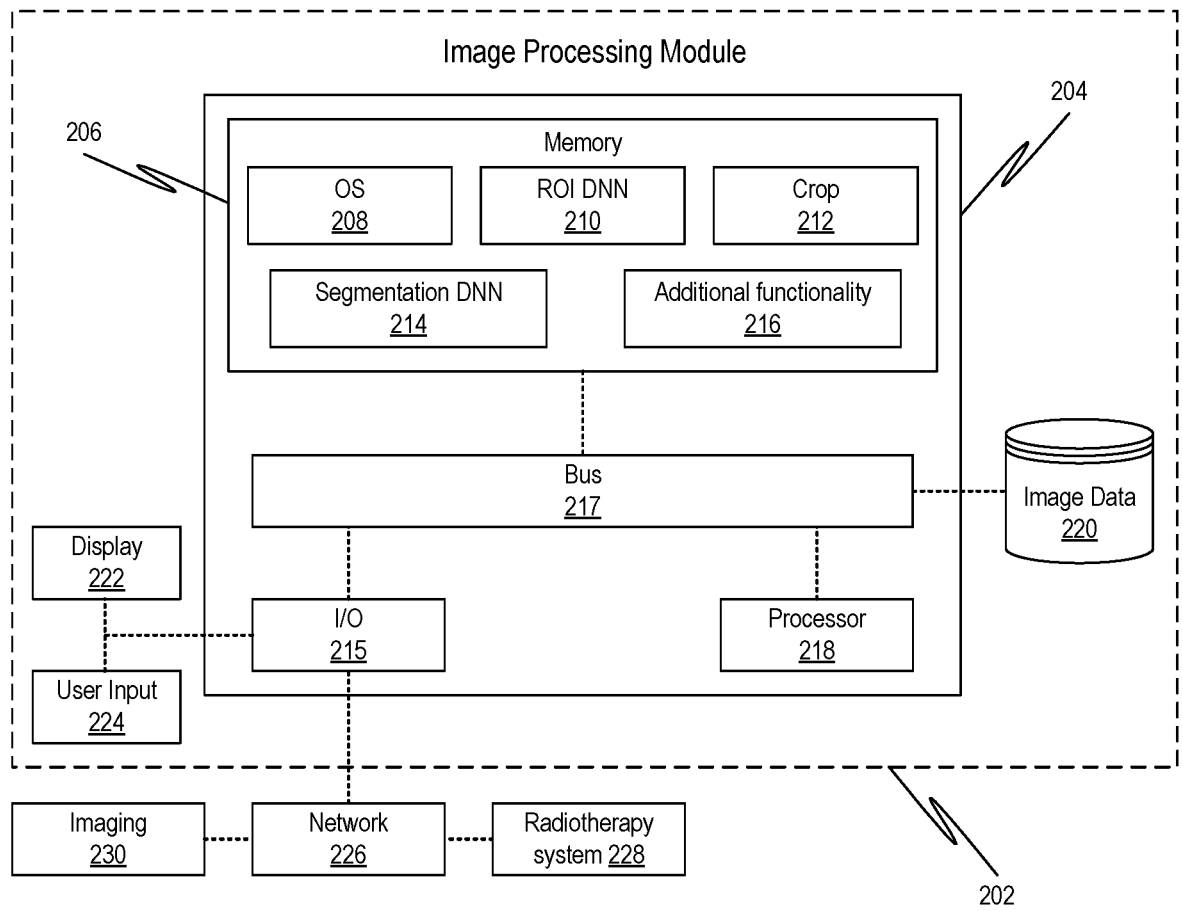
FIG. 2A is a simplified schematic diagram illustrating aspects of a medical image processing and radiotherapy systems, according to various embodiments of the disclosed subject matter.
Figure 2B:
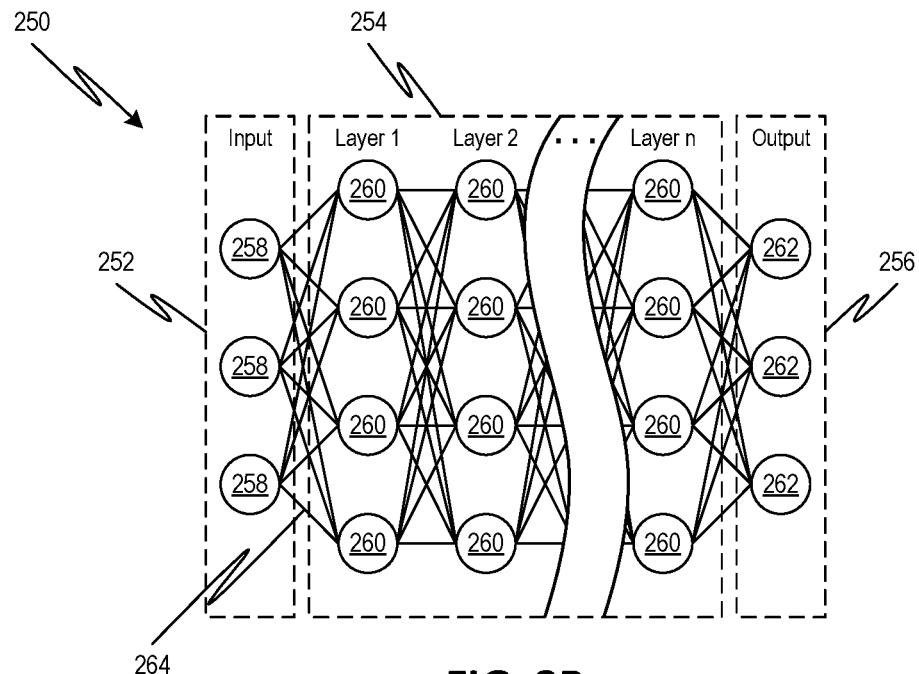
FIG. 2B is a simplified node map of a deep neural network, according to various embodiments of the disclosed subject matter.

For example, FIG. 2B illustrates a simplified node map 250 for an exemplary DNN model. The DNN model includes a stack of distinct layers (vertically oriented in FIG. 2B) that transform an input (provided to the nodes 258 of input layer 252) into an output (at nodes 262 of output layer 256). The intervening layers (Layer 1 through Layer n) between the input layer 252 and output layer 256 are referred to as "hidden" layers 254. At least two hidden layers are provided in order for the neural network to be considered "deep." Each hidden layer has respective nodes 260, which perform a particular computation and are interconnected to nodes in adjacent layers. For example, each node 260 can include a weighting function, which provides weights to respective inputs, and an activation function, which processes the weighted inputs to generate respective outputs. The different hidden layers 254 can include, but are not limited to, final loss layers, non-linear operator layers, pooling layers, subsampling layers, fully connected layers, and convolutional layers. Although FIG. 2B illustrates the hidden layers 254 as having more nodes 260 per layer than a number of the nodes 258/262 in the input 252 and output 256 layers, other numbers and configurations are also possible. Indeed, the simplified map illustrated in FIG. 2B is intended to be exemplary only, and other maps based on a selected DNN (e.g., a convolutional neural networks) are also possible according to one or more contemplated embodiments.

In general, operation of each DNN model involves a training phase and an inference phase. In the training phase, the DNN model uses training data sets of medical images to generate a particular output. For example, the training data set can include 2-D or 3-D images with ground truth contours for the anatomical structures imaged by the different pixels or voxels. For training of the first neural network model, the training data set can include additional ground truth information, such as cut-off plane location and/or user-defined ROIs (e.g., bounding boxes). As used herein, "training" refers to determining one or more parameters of nodes in hidden layers of the DNN model, for example, by an iterative process that varies parameters such that the DNN model output more closely matches corresponding ground truth. For example, nodes 260 in the hidden layer 254 can include a filter or kernel, parameters of which (e.g., kernel weight, size, shape, or structure) can be adjusted during the training process. During the inference phase, the trained DNN models operate on medical image(s) of a patient to automatically process features of the medical image(s) (e.g., to determine an ROI and contours of anatomical structures in the image).

Each respective DNN model may run on a corresponding DNN engine, which refers to any suitable hardware and/or software component(s) of a computer system that is capable of executing algorithms according to any suitable deep learning model. In embodiments, the deep learning model(s) can be based on any existing or later-developed neural network, or combinations thereof. Exemplary neural networks include, but are not limited to, a convolutional neural network (ConvNet or CNN) (e.g., U-Net, deep CNN, LeNet, V-Net, AlexNet, VGGNet, Xception, DenseNet, GoogLeNet/Inception, etc.), residual neural network (ResNet), recurrent neural network (RNN) (e.g., Hopfield, Echo state, independent RNN, etc.), long short-term memory (LSTM) neural network, recursive neural network, generative adversarial neural networks (GANs), and deep belief network (DBN).

The first neural network model (also referred to herein as a region-of-interest deep neural network, or ROI DNN) can be trained using a training set including ground truth contours of anatomical structures with the task of locating specified cut-off planes or an ROI. The ROI can be a bounding box around the anatomical structure or simply a rough estimate of a volume or shape where an anatomical structure is located. During the training phase, this information can be used to crop medical images of a training set, which may be the same or different from the training set of the ROI DNN. These cropped images are used for training the second neural network model (also referred to herein as a segmentation deep neural network, or Segmentation DNN).

Once trained, both the ROI and Segmentation DNNs can be used to analyze medical image(s) of a patient. In particular, the ROI DNN can be applied to the medical image(s) in order to identify cut-off planes or an ROI. The cut-off planes or ROI from the ROI DNN are used to crop the medical image(s) input to the Segmentation DNN, which determines appropriate contours for unknown anatomical structures in the image(s). In some embodiments, while the exact cut-off plane generated by the ROI DNN might not be precise, it nevertheless yields sharp cut-offs on a plane, which may be advantageous in practical applications as it aligns better with clinical practices and may be easier to correct by clinical personnel during contour quality assurance (QA).

For the medical images (whether 2-D or 3-D) of the training sets and/or of the patient, any suitable medical imaging modality or modalities can be used, such as, but not limited to, X-ray, computer tomography (CT), cone beam computed tomography (CBCT), spiral CT, positron emission tomography (PET), magnetic resonance imaging (MRI), functional MRI, single photon emission computed tomography (SPECT), optical tomography, ultrasound imaging, fluorescence imaging, radiotherapy portal imaging, or any combinations thereof. For example, image data may include a series of 2-D images or slices, each representing a cross-sectional view of the patient's anatomy. Alternatively or additionally, image data may include volumetric or 3-D images of the patient, or a time series of 2-D or 3-D images of the patient.

In some embodiments, the disclosed DNN models can operate in combination with a radiotherapy system, for example, as illustrated in FIG. 2A. In particular, FIG. 2A illustrates aspects of a system employing an image processing module 202 with ROI DNN 210 and Segmentation DNN 214. Image processing module 202 may include, for example, a computer system 204 that can implement one or more aspects of the process of FIG. 5A. Although shown as a single module 202, the functionality of module 202 can be implemented as a distributed system or otherwise. Moreover, although illustrated separately, the image processing module 202 and the treatment planning system 318 (FIG. 3) may be integrated together, for example, as a single module with both image processing and treatment planning functionality provided by memory 206, as separate parts of a common computer system 204, or as separate parts of a common system (e.g., a central or distributed processing system operating on a remote server).

For example, the computer system 204 can include a bus 217 or other mechanism for communicating information between components. The computer system 204 can also include a processor 218, for example, a general or specific purpose processor (e.g., graphics processing unit (GPU)), coupled to bus 217. The computer system 204 can include an input/output module 215, for example, a communication device such as a network interface card that provides access to network 226 (which may be the same network by which the image processing module 202 communicates with the radiation therapy system 228), and/or input/output ports that allow a user to interact with the computer system 204, for example via user input devices 224 (e.g., mouse, keyboard, etc.) and display 222. A user can thus interact with computer system 204 directly or remotely through network 226 or via any other method.

The computer system 204 can also include a memory 206 that stores information and instructions to be executed by processor 218. The memory 206 can be comprised of any combination of random access memory (RAM), read only memory (ROM), static storage such as a magnetic or optical disk, or any other type of computer readable media. For example, computer readable media may be any available media that can be accessed by processor 218 and can include both volatile and nonvolatile media, removable and non-removable media, and communication media. Communication media may include computer readable instructions, data structures, program modules or other data in a modulated data signal such as a carrier wave or other transport mechanism and includes any information delivery media.

Memory 206 can store software modules that provide functionality when executed by processor 218. The modules can include, for example, an operating system 208, an ROI DNN model 210, a cropping module 212, a segmentation DNN model 214, and an additional functionality module 216. The operating system 208 can provide operating system functionality for computer system 204. The ROI DNN model 210 can receive medical image data (whether training data or medical image(s) for inference) from database 220, or via I/O 215 and network 226 from medical imaging device 230 or radiotherapy system 228. Based on the received medical image data, the ROI DNN model 210 can generate cropping data. The cropping module 212 receives the cropping data from the ROI DNN model 210 and crops the medical images based thereon. The Segmentation DNN model 214 can receive the cropped medical image data (whether training data or medical image(s) for inference) from the cropping module 212 and can generate contours for anatomical structures in the cropped images. For example, the ROI DNN model 210, the cropping module 212, and the Segmentation DNN model 214 can operate to carry out the functions described below with respect to FIGS. 4A-7.

Configurations and components for the image processing module, the network, the medical imaging device, and the radiation therapy systems other than those specifically illustrated in FIG. 2A are also possible according to one or more contemplated embodiments. Moreover, although illustrated as separate modules 210-216, embodiments may combine functionality into a single module or group of modules. For example, features of the cropping module 212 may be integrated with, and thus form a part of, the segmentation DNN model 214. Other variations and combinations will be readily apparent to one of ordinary skill in the art.

Figure 3:
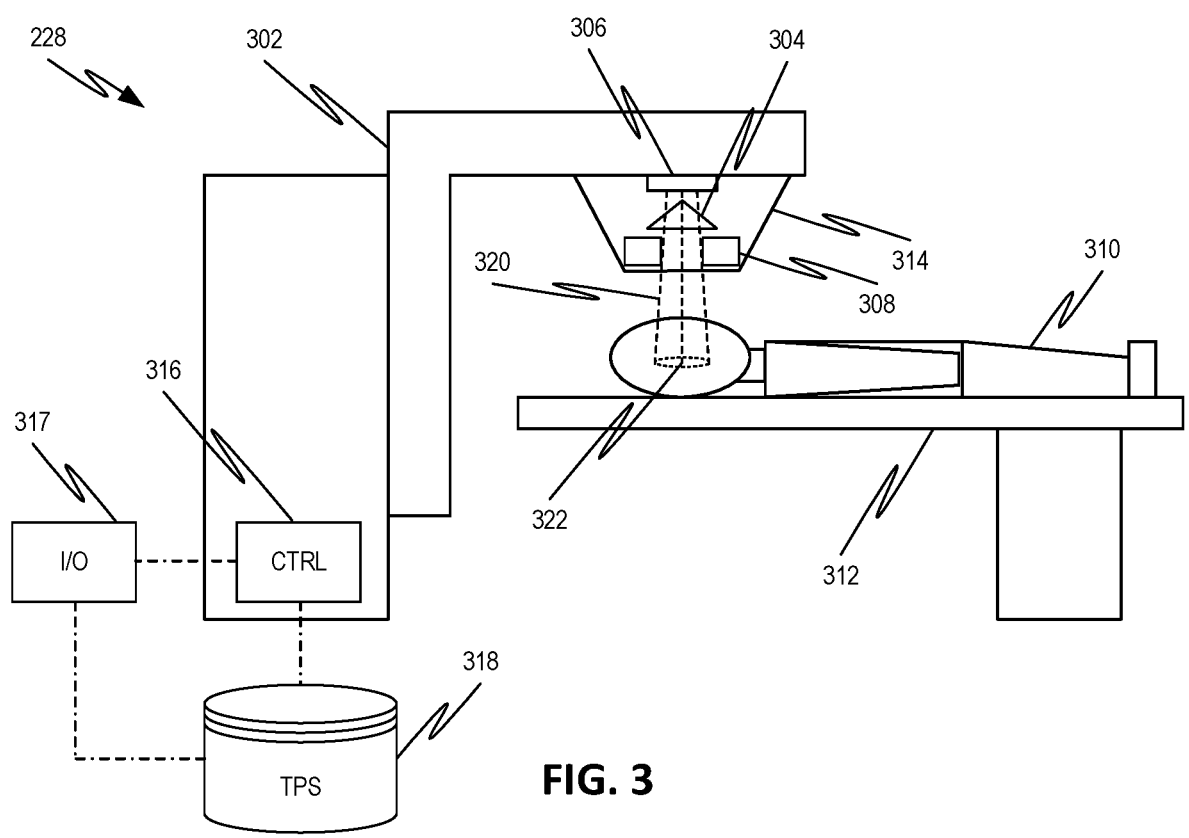
FIG. 3 illustrates aspects of a radiation therapy system, according to various embodiments of the disclosed subject matter.

Referring to FIG. 3, an exemplary radiation therapy system 228 for use with the image processing module 202 is shown. The therapy system 228 can provide radiation to a patient 310 positioned on a treatment couch 312 and can allow for the implementation of various radiation dose verification protocols. The radiation therapy can include photon-based radiation therapy, particle therapy, electron beam therapy, or any other type of treatment therapy.

In an embodiment, the radiation therapy system 228 can be a radiation treatment device such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 228 has a gantry 302 supporting a radiation treatment head 314 with one or more radiation sources 306 (e.g., target) and various beam modulation elements, such as, but not limited to, flattening filter 304 and collimating components 308. The collimating components 308 can include, for example, a multi-leaf collimator (MLC), upper and lower jaws, and/or other collimating elements. The collimating components 308 and/or the flattening filter 304 can be positioned within the radiation beam path by respective actuators (not shown), which can be controlled by controller 316.

The gantry 302 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 314 at various rotational and/or axial positions relative to the patient 310 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 308, which can be a computer-controlled mechanical beam shaping device attached to the head 314 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively or additionally, the radiation therapy device can be a tomotherapy device where intensity modulation is achieved with a binary collimator (not shown) which opens and closes under computer control (e.g., control 316). As the gantry 302 continuously rotates around the patient 310, the exposure time of a small width of the beam can be adjusted with opening and closing of the binary collimator, allowing radiation to be delivered to the treatment volume 322 through the most desirable directions and locations of the patient 310.

Alternatively or additionally, the radiation therapy device can be a helical tomotherapy device that includes a slip-ring rotating gantry, or an intensity modulated arc therapy device (IMAT) that uses rotational cone beams of varying shapes to achieve intensity modulation instead of rotating fan beams. In still another alternative, the radiation therapy device can be a simplified intensity modulated arc therapy (SIMAT) device which uses multiple arcs, or a sweeping window arc therapy device (SWAT), which sweeps the MLC leaf positions across the target planning volume (TPV) with rotation. In yet another alternative, the radiation therapy device can be a volumetric modulated arc therapy (VMAT) device where dose rate, beam aperture shape, and the speed of rotation can be continuously varied to deliver the prescribed dose to the TPV. In yet another alternative, the radiation therapy device can be a volumetric high-definition (or hyperarc) therapy (HDRT) device where does rate, beam aperture shape, speed of rotation and orientation of the patient support can be continuously varied to deliver the prescribed does to the TPV. Indeed, any type of IMRT device can be employed as the radiation therapy device of system 228. For example, embodiments of the disclosed subject matter can be applied to image-guided radiation therapy (IGRT) devices. Each type of radiation therapy device can be accompanied by a corresponding radiation plan and radiation delivery procedure.

The controller 316 can include a computer with appropriate hardware such as a processor, and an operating system for running various software programs and/or communication applications. The controller 316 can include software programs that operate to communicate with the radiation therapy device, which software programs are operable to receive data from external software programs and hardware. The computer can also include any suitable input/output (I/O) devices 317, which can be adapted to allow communication between controller 316 and a user of the radiation therapy system 228, e.g., medical personnel, such as a radiation oncologist or radiation therapist. For example, the controller can be provided with I/O interfaces, storage devices, memory, keyboard, mouse, monitor, printers, scanner, etc.

Alternatively or additionally, the I/O devices 317 can provide access to a network (not shown) for transmitting data between controller 316 and remote systems. For example, the controller 316 can be networked via I/O 317 with other computers, e.g., computer 202. Both the radiation therapy device 228 and the controller 316 can communicate with a network (e.g., network 226) as well as databases and servers, for example, a dose calculation server (e.g., distributed dose calculation framework) and/or a treatment planning system 318 and/or a radiation therapy management system. The controller 316 may also be configured to transfer medical image related data between different pieces of medical equipment.

The system 228 can also include a plurality of modules containing programmed instructions (e.g., as part of controller 316, or as separate modules within system 228, or integrated into other components of system 228), which instructions cause system 228 to perform different functions related to radiation therapy/surgery and/or treatment planning when executed. Although image processing module 202 is shown separate from radiotherapy system 228 in FIG. 2A, it is also possible for image processing module 202 to be integrated with the radiotherapy system 228, for example, as part of controller 316. Computer program code for carrying out operations as described herein may be written in any programming language, for example, C or C++ programming language.

Although the discussion of FIGS. 2A and 3 above has focused on the use of the image processing module 202 with a radiotherapy system 228, embodiments of the disclosed subject matter are not limited thereto. Indeed, the image processing module 202 may be provided as a separate independent system for image analysis, may be integrated with an imaging modality 230, may communicate with other medical treatment systems, or may be integrated with other medical treatment systems. Accordingly, embodiments of the disclosed image processing module are not limited to the specific configuration illustrated in FIG. 2A or limited to use with radiotherapy systems.

Figure 4A:
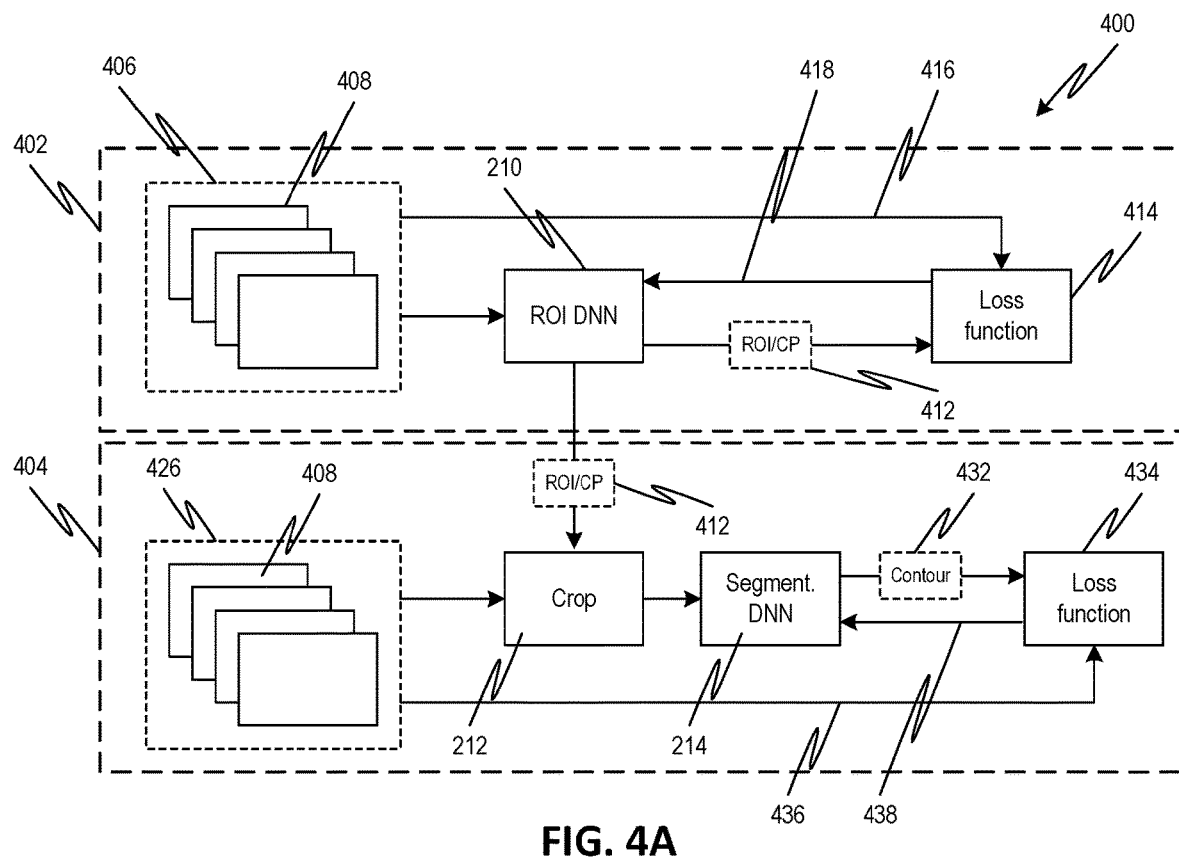
FIG. 4A is a simplified schematic diagram of operation of first and second neural network models during a training phase, according to various embodiments of the disclosed subject matter.
Figure 4B:
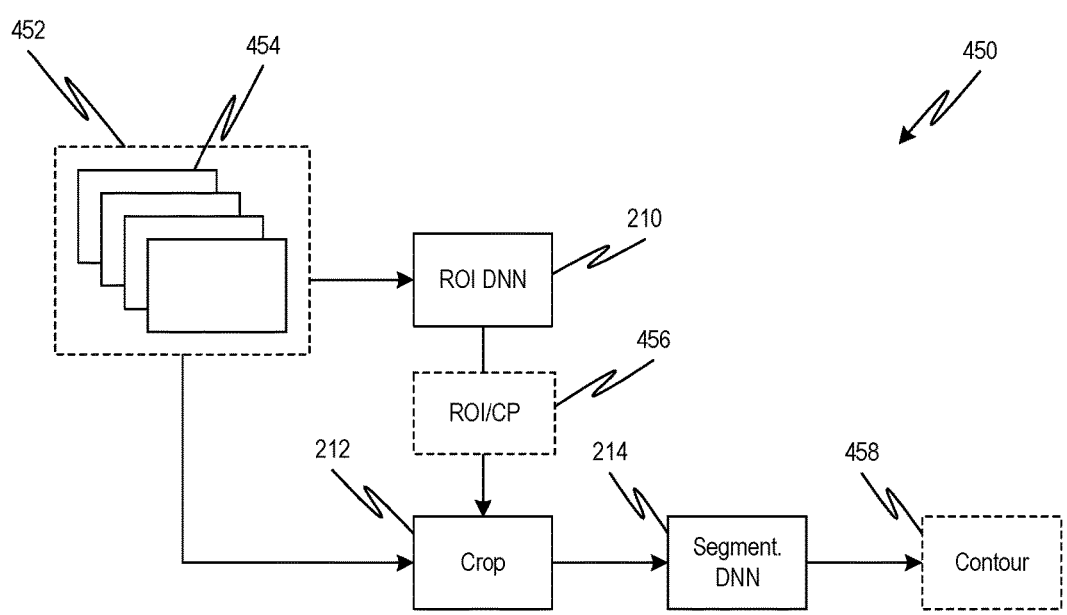
FIG. 4B is a simplified schematic diagram of operation of first and second neural network models during an inference phase, according to various embodiments of the disclosed subject matter.
Figure 5A:
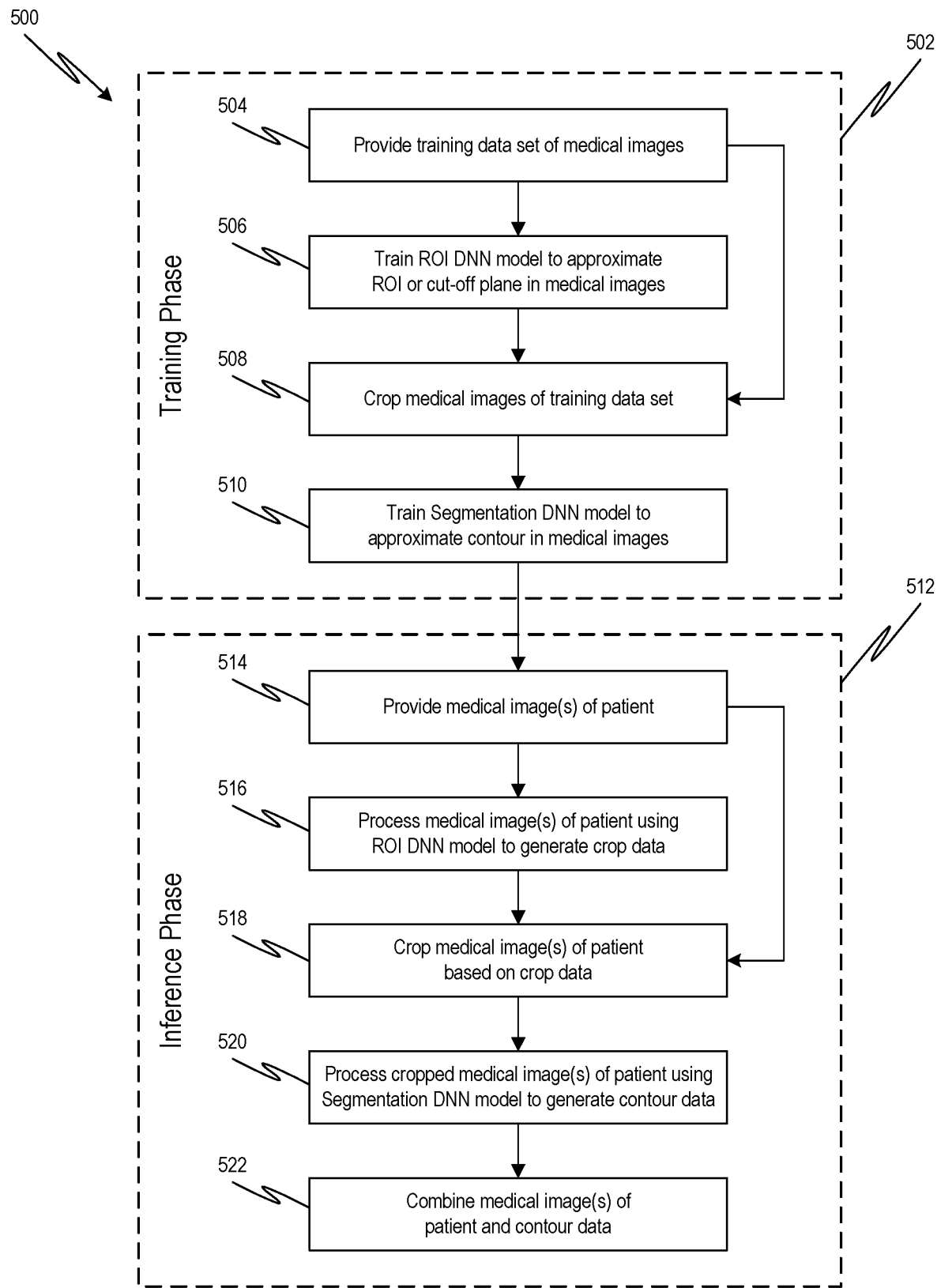
FIG. 5A is a process flow diagram for generalized training and inference phases of first and second neural network models, according to various embodiments of the disclosed subject matter.
Figure 5B:
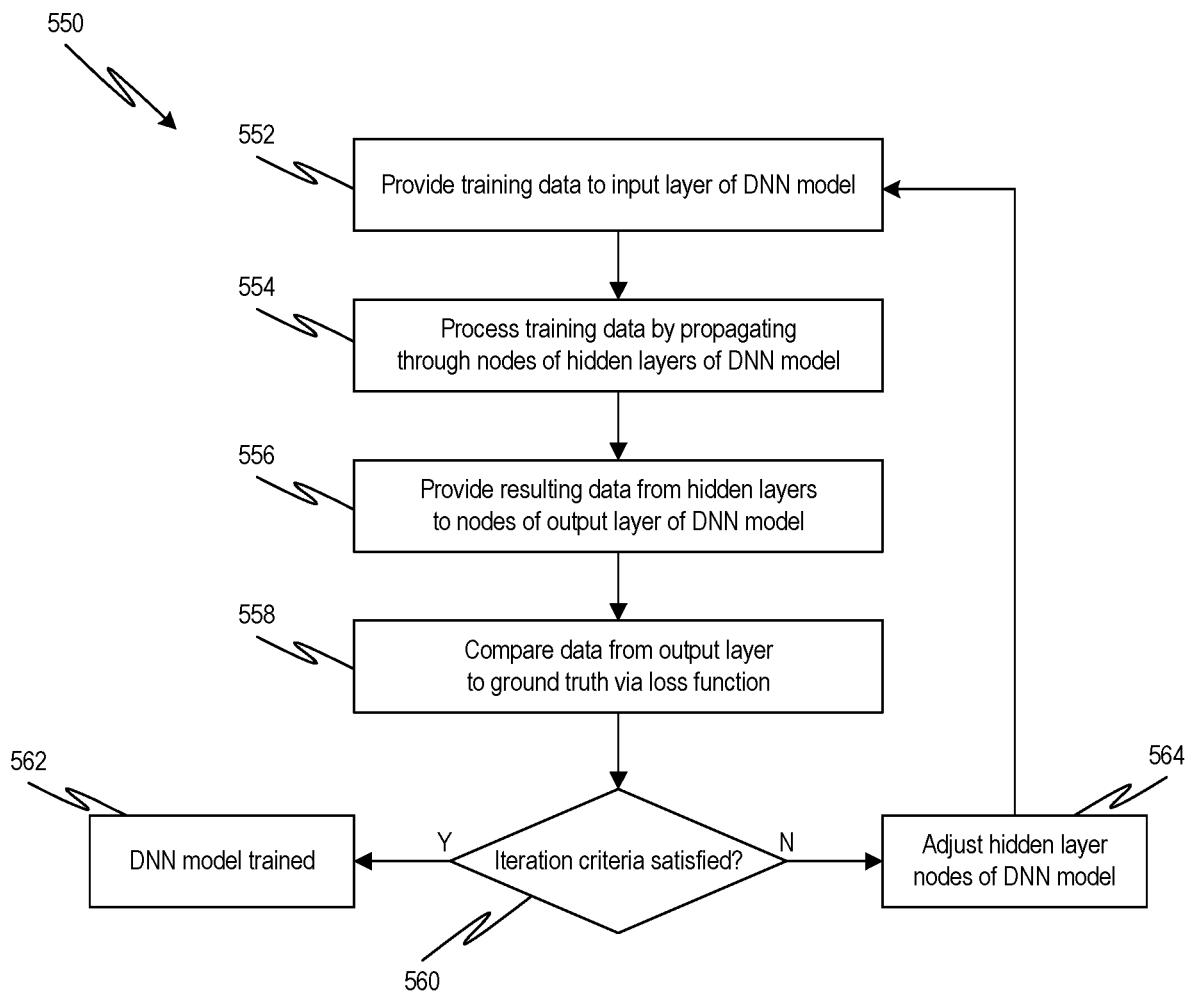
FIG. 5B is a process flow diagram for details of the training phases of the first and second neural network models, according to various embodiments of the disclosed subject matter.

Referring to FIGS. 4A-5B, exemplary operation of the ROI and Segmentation DNN models will now be described. FIG. 4A is a schematic illustrating operation of the ROI and Segmentation DNN models during a training phase 502. FIG. 4B is a schematic illustrating operation of the ROI and Segmentation DNN models during an inference phase 512. FIG. 5A is a process flow diagram of various steps performed during training 502 and inference 512 phases, while FIG. 5B is a generalized process flow diagram for various steps underlying the training of each DNN model in FIG. 5A.

In FIG. 5A, the process 500 can begin with the training phase 502, which trains each DNN model on an appropriate training data set. In some embodiments, for example, where the ROI and Segmentation DNN models have been previously trained, the training phase 502 can be omitted and the process 500 can proceed directly to the inference phase 512 for use in processing medical image(s) of a patient.

In training phase 502, the image processing module can have a setup 400 as illustrated in FIG. 4A. The process 500 can begin at 504, where a training data set 406 of medical images 408 is provided. The training data set 406 can also include desired output, in the form of ground truth, e.g., contours, bounding boxes around contours, and/or cut-off planes (i.e., plane where contouring should stop) that are verified by an expert or system user. For example, the training data 406 can be user-generated through observations and experience to facilitate supervised learning and may be extracted from past images of previous patients. Preferences of the user or facility can thus be taken into account in the processing by virtue of the user-defined training data set 406. Alternatively or additionally, the training data set 406 can be pre-processed using any suitable data augmentation approach (e.g., rotation, flipping, translation, scaling, noise addition, cropping, or combinations thereof) to produce a new training data set with modified properties that may improve model generalization.

In some embodiments, the training data set 406 can include additional subsets. For example, data set 406 can include a validation set that is used to track the quality of the model 210 during training thereof (e.g., at 560 in FIG. 5B), but is not otherwise used as input to the model 210 during training. Alternatively or additionally, the training data set 406 can include a test subset that is only used after training to quantify the quality of the trained model 210 (e.g., accuracy, dice score) and/or to verify that the model 210 has not over-learned or under-learned the data.

In training phase 502, the process 500 can proceed to 506, where training of the ROI DNN model 210 occurs. The ROI DNN model 210 can be trained to output either ROI or cut-off plane, but not necessarily both. Indeed, in some embodiments, it may be sufficient to only estimate the cut-off plane rather than ROI. In other embodiments, a bounding box or ROI around the organ or other anatomical structure may be desired. In any event, the selected output will result in separate models and require separate training. In some embodiments, separate ROI DNN models can be simultaneously or sequentially trained, e.g., one model designed to output a bounding box or ROI and the other model to output a cut-off plane. In such cases, the outputs from the separate ROI DNN models can be combined to crop the images for input to the Segmentation DNN model.

Training 506 of the ROI DNN model 210 can be according to the process flow 550 of FIG. 5B and can be represented by the layout 402 of FIG. 4A. In particular, at 552, the training data set 406 is input to the ROI DNN model 210, for example, to its input layer. At 554, the ROI DNN model 210 processes the training data by propagating through nodes of its hidden layers. At 556, the ROI DNN model 210 produces an output 412 (e.g., bounding box, ROI, or cut-off plane) at its respective output layer, which output 412 can be compared to ground truth cut-off or ROI 416 via a loss function 414 at 558. For example, loss function 414 can be mean-squared error, dice loss, cross entropy-based losses or any other loss function known in the art.

During the training 550, the model 210 is given feedback 418 (by loss function 414) on how well its output 412 matches the correct output 416. Once an iteration criteria is satisfied at 560 (e.g., loss function 414 meets a predetermined threshold, a threshold number of iterations has been reached, or no further improvement is seen between iterations), the ROI DNN model 210 is fixed at 562. Otherwise, the training 550 proceeds to 564, where the model 210 is modified, e.g., by adjusting parameters of the hidden layer nodes, in order to improve the match between output 412 and the desired output 416. The training process 550 can iterate repeatedly until the desired iteration criteria is met at 560.

In some embodiments, the loss function 414 can be modified to reduce the impact of the cut-off plane during training 506. This can force the ROI DNN model 210 to produce a cut-off plane (e.g., axial slices) more accurately, but may reduce the impact of the exact position of the cut-off plane. Alternatively or additionally, some parameters can be defined and adjusted at 552 in order to only impact training 550 without otherwise affecting inference, such as, but not limited to, loss function, hyper parameters (e.g., dropout, regularization), training data augmentation (e.g., to avoid overlearning and achieve better generalization), and preprocessing of input data (e.g., scaling, normalization).

Returning to FIG. 5A, the process 500 can proceed to 508, where the medical images 408 of the training data set 426 are cropped by cropping module 212 based on the output 412 from the ROI DNN model 210. For example, the output 412 can include parameters (e.g., planes, 2-D or 3-D coordinates (Cartesian, cylindrical, or spherical coordinates), etc.) that the cropping module 212 translates into cropping actions for images 408. The cropping 508 by the cropping module 212 may be such that the cropping stops at the border of the organ or other anatomical structure with no or minimal margins. This can help to enforce a sharp edge in contours eventually produced by the Segmentation DNN model 214.

Note that the training data set 426 may be identical to training set 406 or may be slightly different than training set 406. For example, training data set 426 may include different ground truth information than the training data set 406, or only a subset of the ground truth information otherwise found in training data set 406. In some embodiments, the training data set 426 includes 3-D image(s) 408 and its corresponding 3-D ground truth label map that associates an anatomical structure to each of the voxels of the 3-D image(s). In some embodiments, the 3-D image(s) 408 may be divided into a sequential stack of adjacent 2-D images, and the 3-D ground truth label map can include sequential 2-D ground truth label maps, respectively corresponding to the sequential stack of adjacent 2-D images. The training data set 426 can have images that have already been segmented (i.e., contoured), where a ground truth label map provides a known anatomical structure label for each pixel of a representative image slice of the training image. In other words, pixels of the ground truth label map can be associated with known anatomical structures.

In some embodiments, the training data set 426 can include additional subsets. For example, data set 426 can include a validation set that is used to track the quality of the model 214 during training thereof (e.g., at 560 in FIG. 5B), but is not otherwise used as input to the model 214 during training. Alternatively or additionally, the training data set 426 can include a test subset that is only used after training to quantify the quality of the trained model 214 (e.g., accuracy, dice score) and/or to verify that the model 214 has not over-learned or under-learned the data.

After cropping 508, the process 500 can proceed to 510, where training of the Segmentation DNN model 214 occurs. The Segmentation DNN model 214 can be trained to output contours 432 for anatomical structures in the cropped medical images 408. Training 510 of the Segmentation DNN model 214 can also be according to the process flow 550 of FIG. 5B and can be represented by the layout 404 of FIG. 4A. In particular, at 552, the cropped images 408 of the training data set 426 are output from the cropping module 212 to the Segmentation DNN model 214, for example, to its input layer. At 554, the Segmentation DNN model 214 processes the cropped images by propagating through nodes of its hidden layers. At 556, the Segmentation DNN model 214 produces an output 432 (e.g., contours of anatomical structures) at its respective output layer, which output 432 can be compared to ground truth contours 436 via a loss function 434 at 558. For example, loss function 434 can be mean-squared error, dice loss, cross entropy-based losses or any other loss function known in the art.

During the training 550, the model 214 is given feedback 438 (by loss function 434) on how well its output 432 matches the correct output 436. The aim of training 550 is to train Segmentation DNN model 214 to perform automatic segmentation of anatomical structures in the image(s) by mapping input data (i.e., cropped images from module 212) to example output data (i.e., ground truth contours 436). In some embodiments, training 550 can involve finding weights that minimize the training error (e.g., as determined by loss function 434) between ground truth contours 436 and estimated contours 432 generated by deep learning engine, and in particular, to define contours with straight edges (or flat surfaces) at the border of the ROI or on a cut-off plane.

In practice, Segmentation DNN model 214 may be trained to identify multiple targets and OARs of any suitable shape or size.

Once an iteration criteria is satisfied at 560 (e.g., loss function 434 meets a predetermined threshold, a threshold number of iterations has been reached, or no further improvement is seen between iterations), the Segmentation DNN model 214 is fixed at 562. Otherwise, the training 550 proceeds to 564, where the model 214 is modified, e.g., by adjusting parameters of the hidden layer nodes, in order to improve the match between output 432 and the desired output 436. The training process 550 thus can iterate repeatedly until the desired iteration criteria is satisfied at 560.

In some embodiments, the loss function 434 can be modified (with or without corresponding modification of loss function 414) to reduce the impact of the cut-off plane during training 510. This may reduce the impact of the exact position of the cut-off plane in the training of the Segmentation DNN model 214. Alternatively or additionally, some parameters can be defined and adjusted at 552 in order to only impact training 550 of Segmentation DNN model 214 without otherwise affecting inference, such as, but not limited to, loss function, hyper parameters (e.g., dropout, regularization), training data augmentation (e.g., to avoid overlearning and achieve better generalization), and preprocessing of input data (e.g., scaling, normalization).

Although the training of the ROI DNN model 210 generates cropping data for use in cropping of the training images for the Segmentation DNN model 214, the models 210 may be considered to be trained separately, i.e., with the training 506 (as illustrated by layout 402 in FIG. 4A) concluding before the training 510 (as illustrated by layout 404 in FIG. 4A) begins. Alternatively or additionally, the training 506 may be concurrent with the training 510, for example, with the output 412 from each iteration of ROI DNN model 210 provided as cropping data for a corresponding iteration of the Segmentation DNN model 214.

In some embodiments, the training data set 426 can optionally include definitions of cut-off planes in the images 408. Since the cut-off plane might not be accurately defined by the imaging information alone, the cut-off plane definitions provided to the Segmentation DNN model 214 can further encourage model 214 to deliver sharp (i.e., flat or straight) cut-offs. Since the training of the Segmentation DNN model 214 is performed to create a model producing sharp cut-offs, the model 214 will subsequently produce sharp cut-offs during the inference phase, even if less accurate ROI definitions are produced by the ROI DNN model 210.

In some embodiments, the providing of the training data set at 504 can include modifying the training data set to improve consistency thereof, for example, by processing the various medical images 408 of data set 406 or data set 426. However, such processing may be time-intensive as it would require manual processing by the user, as well as re-training of models 210, 214 after each correction to see if the outputs 412, 432 are improved.

In some embodiments, the training 506 of the ROI DNN model 210 can be based on anatomical landmarks, such as bones. However, for certain anatomies, this may enforce an ROI with minimal ability to adapt to different patient anatomies. For example, with respect to the superior breast, the ROI DNN model 210 can be trained to crop based on the half-way point in an axial direction between the trachea bifurcation and the upper border of the lung. Even though this may be a mean cutting point, it would not take into account different patient anatomies.

Returning to FIG. 5A, once training phase 502 has completed, the process 500 can proceed to the inference phase 512, which uses the trained DNN models to process medical image(s) of a patient to automatically segment (i.e., contour) unknown anatomical structures shown therein. In inference phase 512, the image processing module can have a setup 450 as illustrated in FIG. 4B. The process 500 can begin 514, where a patient data set 452 including one or more medical image(s) 454 are provided to the trained ROI DNN model 210 and the cropping module 212. The image(s) of the patient can be obtained using any medical imaging modality and do not necessarily need to be of the same modality as images used to train the DNN models 210, 214.

Process 500 can then proceed to 516, where the medical image(s) 454 are processed by the trained ROI DNN model 210. The ROI DNN model 210 thus outputs either ROI or cut-off plane data 456 based on its training, which data 456 is used by cropping module 212 to crop the medical image(s) 454 at 518. For example, the data 456 can include parameters (e.g., planes, 2-D or 3-D coordinates (Cartesian, cylindrical, or spherical coordinates)) that the cropping module 212 translates into cropping actions for images 454.

The process 500 can proceed to 520, where the cropped medical image(s) are processed by the trained Segmentation DNN model 214. The Segmentation DNN model 214 thus outputs contour data 458 based on its training. For example, at least one of the generated contours in data 458 can have a substantially straight edge or substantially flat surface at a corresponding boundary or cut-off plane. In some embodiments, the contour data 458 may be combined with the original medical image(s) at 522, such that the contours are overlaid on the corresponding anatomical structures in the image, for example, for visualization by a user or for use in radiation treatment planning. Alternatively, the Segmentation DNN model 214 may directly produce the contours on the medical images as an output without separate combination step 522.

Figure 6:
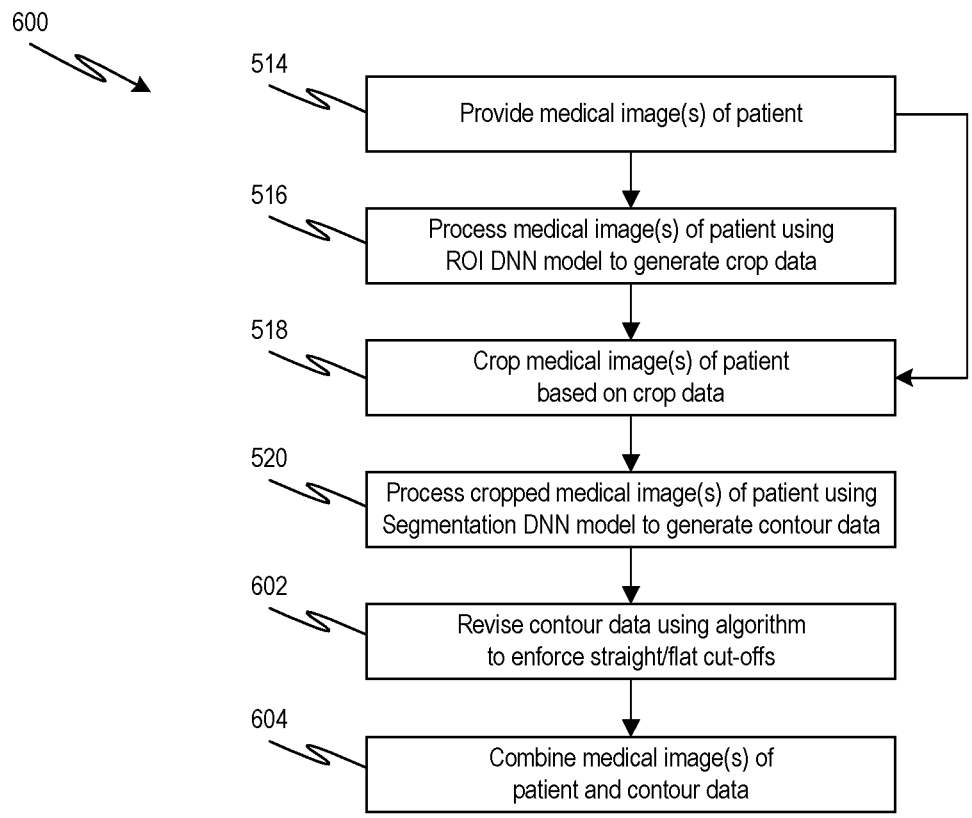
FIG. 6 is a process flow diagram for generalized inference phases of the first and second neural network models employing algorithm-enforced straight or flat cut-offs, according to various embodiments of the disclosed subject matter.

Various modifications of the layouts and processes illustrated in FIGS. 4A-5B are also possible according to one or more contemplated embodiments. For example, in some embodiments, post-processing in the inference phase, which is separate from the processing by the DNN models 210, 214, can be provided to enforce the straight/flat cut-offs in generated contours. FIG. 6 illustrates a process flow 600 for such post-processing. Process 600 involves steps 514-520 similar to those of inference phase 512 of FIG. 5A. In contrast to FIG. 5A, after the contour data is generated by the Segmentation DNN model at 520, the process 600 proceeds to 602, where the generated contour data is revised using an algorithm that enforces straight/flat cut-offs. For example, the algorithm could be a heuristic algorithm. The algorithm-modified contour data could then be combined with the original medical image(s) at 604, such that the contours are overlaid on the corresponding anatomical structures in the image, for example, for visualization by user or use in radiation treatment planning. Alternatively, the Segmentation DNN model 214 may directly produce the contours on the medical images as an output, and the algorithm can directly modify the contours on the medical images, without necessarily requiring a separate combination step 604.

Figure 7:
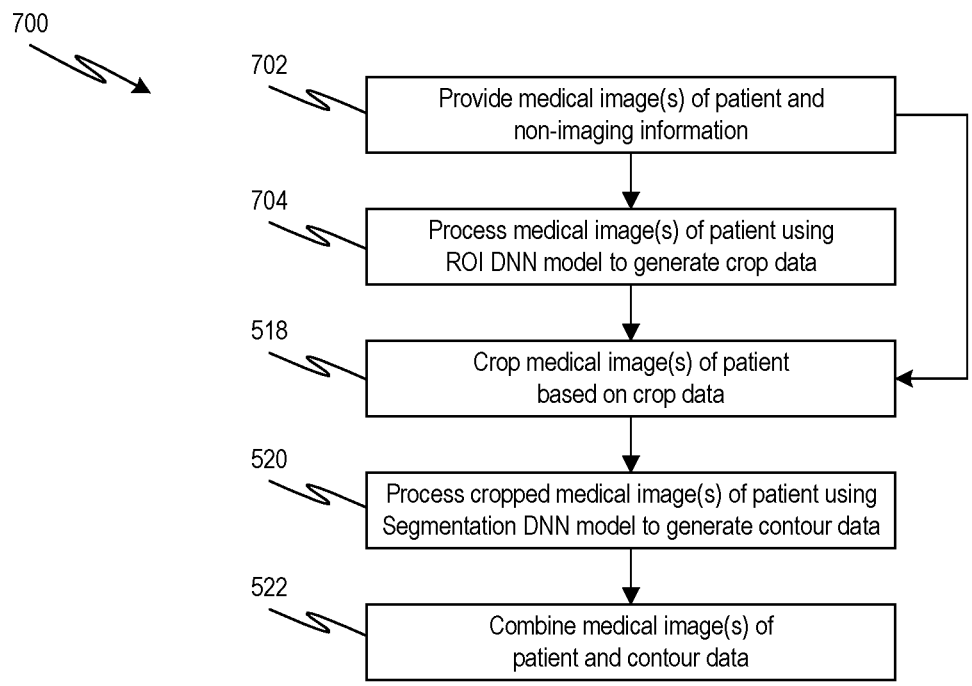
FIG. 7 is a process flow diagram for generalized inference phases of the first and second neural network models additionally employing non-imaging information, according to various embodiments of the disclosed subject matter.

Alternatively or additionally, in some embodiments, non-imaging information can be used along with the medical image(s) of the patient in the inference phase. For example, non-imaging information, such as field parameters for a planned radiotherapy, can be used to define appropriate cutting planes. In radiotherapy planning, the out of field part of anatomical structures might not be of interest, depending on if the organ is serial or parallel. The out of field cut-off plane can be detected if the field geometry is known. FIG. 7 illustrates a process flow 700 for inference phase processing using non-imaging information. In particular, at 702, the one or more medical image(s) 454 can be provided along with the non-imaging information. The non-imaging information can be provided to the trained ROI DNN model 210, for example, for use in generating cropping data at 704. Alternatively or additionally, the non-imaging information can be provided to the cropping module 212 for use in cropping the medical image(s) 454, independent of or in combination with cropping data from model 210. Alternatively or additionally, the non-imaging information can be provided to the trained Segmentation DNN model 214 for use in generating the contour data 458. Otherwise, process 700 can involve steps 518-522 similar to those described above for the inference phase 512 of FIG. 5A.

Although a single ROI DNN model 210 and single Segmentation DNN model 214 are illustrated in FIGS. 4A-4B and discussed with respect to FIGS. 5A-7, embodiments of the disclosed subject matter are not limited thereto. For example, contours can be generated by employing one or more Segmentation DNN models, working separately or in unison. For example, outputs from separate Segmentation DNN models can be combined together to form a singular output of contour data. In such a configuration, each Segmentation DNN model may have different operating characteristics, such as a different input image resolution, different hidden layer configuration, or different underlying neural network models (e.g., CNN versus RNN, etc.). The cropping based on ROI DNN model output may be with respect to images input to each Segmentation DNN model, input to only one of the Segmentation DNN models, or input to only a subset of the Segmentation DNN models. Alternatively or additionally, multiple ROI DNN models can be provided, for example, to separately determine ROI and cutoff planes. The output from each ROI DNN model may be combined together to generate a single output of cropping instructions or used separately by cropping module, for example, to crop images input to particular Segmentation DNN models differently from images input to other Segmentation DNN models. Other variations and modifications will be readily apparent to one of ordinary skill in the art.

It will be appreciated that a method is described, comprising: training at least one first neural network model using a first data set of medical images, each of the medical images in the first data set including a contour of an anatomical structure therein and at least one of a region-of-interest (ROI) around the anatomical structure and a cut-off plane with respect to the anatomical structure, each first neural network model being trained to approximate the ROI or the cut-off plane; based on data from the at least one first neural network model, cropping medical images of a second data set, each of the medical images in the second data set including a contour of the anatomical structure; and training at least one second neural network model using the cropped medical images, each second model being trained to approximate the contour of the anatomical structure.

In embodiments, the medical images of the first and second data sets are the same.

In embodiments, the method further comprises: processing a third data set of medical images using the at least one first neural network model to generate cropping data; cropping the third data set of medical images based at least on the cropping data from the at least one first neural network model; and processing the cropped third data set of medical images using the at least one second neural network model to generate one or more contours of anatomical structures in the third data set of medical images.

In embodiments, at least one of the generated contours has a substantially straight edge or substantially flat surface.

In embodiments, the method may further comprise, after processing by the at least one second neural network model, processing the third data set of medical images using at least one algorithm that modifies the generated contours to have a substantially straight edge or substantially flat surface.

In embodiments, the at least one algorithm comprises a heuristic algorithm.

In embodiments, the method may further comprise developing a treatment plan for radiotherapy based at least on the third data set of medical images and the generated contours.

In embodiments, the cropping the third data set of medical images is further based on an irradiation field placement of the radiotherapy.

In embodiments, the training the at least one second neural network model also uses definitions of cut-off planes in the medical images of the second data set.

In embodiments, the training of the at least one first neural network model is a process that iterates until a first loss function meets first predetermined criteria, the training of the at least one second neural network model is a process that iterates until a second loss function meets second predetermined criteria, and further comprising modifying one of the first and second loss functions to change an effect of the cut-off plane during the respective training.

In embodiments, the at least one first neural network model is trained to approximate the ROI based on an anatomical landmark.

In embodiments, the contour of the anatomical structure in the first data set or the second data set is custom defined by a user.

In embodiments, each of the first and second neural network models is a deep neural network having more than two hidden layers.

In embodiments, the anatomical structure in the first data set or the second data set comprises an organ to be irradiated or an organ-at-risk.

It will also be appreciated that a system is disclosed to apply the methods of any one or a combination of the above recited embodiments.

It will also be appreciated that a system is disclosed, comprising: one or more data storage devices storing at least one first neural network model and at least one second neural network model, each first neural network model having been trained to approximate a region-of-interest (ROI) around an anatomical structure or a cut-off plane with respect to the anatomical structure, each second neural network model having been trained to approximate a contour of the anatomical structure; and one or more processors operatively coupled to the one or more data storage devices and configured to: employ the at least one first neural network model to process one or more medical images of a patient to generate cropping data; based at least one the cropping data from the at least one first neural network model, crop the one or more medical images of the patient; and employ the at least one second neural network model to process the one or more cropped medical images of the patient to generate one or more contours of anatomical structures in the medical images of the patient.

In embodiments, the one or more processors is further configured to: train the at least one first neural network model to approximate ROIs or cut-off planes using a first data set of medical images, each of the medical images of the first data set including a contour of an anatomical structure therein and at least one of a ROI around the anatomical structure or a cut-off plane with respect to the anatomical structure; based on data from the first neural network model, crop medical images of a second data set, each of the medical images of the second data set including a contour of anatomical structure therein; and train the at least one second neural network model to approximate contours of anatomical structures using the cropped medical images of the second data set.

In embodiments, at least one of the generated contours has a substantially straight edge or substantially flat surface.

In embodiments, the system may further comprise: a radiotherapy device configured to deliver radiation treatment to a patient, wherein the one or more processors are further configured to control the radiotherapy device to irradiate the patient according to a treatment plan based at least on the one or more medical images of the patient and the generated contours.

In embodiments, the one or more processors is further configured to, using at least one algorithm, process the one or more medical images of the patient to modify the generated contours to have a substantially straight edge or substantially flat surface.

In embodiments, the at least one algorithm comprises a heuristic algorithm.

In embodiments, the one or more processors is configured to crop the one or more medical images of the patient based on an irradiation field placement of a radiotherapy.

In embodiments, the one or more processors is configured to train the at least one second neural network model using definitions of cut-off planes in the medical images of the second data set.

In embodiments, the one or more processors is configured to: train the at least one first neural network model by an iterative process and calculate a first loss function after each iteration; train the at least one second neural network model by an iterative process and calculate a second loss function after each iteration; and receive input to modify one of the first and second loss functions prior to or during the respective iterative process to change an effect of the cut-off plane in the respective training.

In embodiments, the one or more processors is configured to train the at least one first neural network model to approximate the ROI based on an anatomical landmark.

In embodiments, each of the first and second neural network models is a deep neural network having more than two hidden layers.

It will also be appreciated that a non-transitory computer-readable storage medium is also disclosed upon which is embodied a sequence of programmed instructions, and a computer processing system that executes the sequence of programmed instructions embodied on the computer-readable storage medium to cause the computer processing system to execute any one or a combination of the herein described method steps, using a system as described herein.

In embodiments, the non-transitory computer-readable storage medium is also disclosed upon which is embodied a sequence of programmed instructions, and a computer processing system that executes the sequence of programmed instructions embodied on the computer-readable storage medium to cause the computer processing system to: process one or more medical images of a patient using at least one first neural network model to generate cropping data, each first neural network model having been trained to approximate a region-of-interest (ROI) around an anatomical structure or a cut-off plane with respect to the anatomical structure; crop the one or more medical images of the patient based at least on the cropping data from the at least one first neural network model; and process the one or more cropped medical images of the patient using at least one second neural network model to generate one or more contours of anatomical structures in the one or more medical images of the patient, each second neural network model having been trained to approximate contours of anatomical structures.

In embodiments, the execution of the sequence of programmed instructions further causes the computer processing system to: train the at least one first neural network model using a first data set of medical images, each of the medical images in the first data set including a contour of an anatomical structure therein and at least one of a region-of-interest (ROI) around the anatomical structure or a cutoff plane with respect to the anatomical structure; based on data from the at least one first neural network model, crop medical images of a second data set, each of the medical images in the second data set including a contour of the anatomical structure; and train the at least one second neural network model using the cropped medical images.

In embodiments, at least one of the generated contours has a substantially straight edge or substantially flat surface.

In embodiments, the execution of the sequence of programmed instructions further causes the computer processing system to: process the one or more medical images of the patient using at least one algorithm that modifies the generated contours to have a substantially straight edge or substantially flat surface.

In embodiments, the at least one algorithm comprises a heuristic algorithm.

In embodiments, the execution of the sequence of programmed instructions causes the computer processing system to crop the one or more medical images of the patient based on an irradiation field placement of a radiotherapy.

In embodiments, the execution of the sequence of programmed instructions causes the computer processing system to train the at least one second neural network model using definitions of cut-off planes in the medical images of the second data set.

In embodiments, the execution of the sequence of programmed instructions causes the computer processing system to: train the at least one first neural network model by an iterative process and calculate a first loss function after each iteration; train the at least one second neural network model by an iterative process and calculate a second loss function after each iteration; and receive input to modify one of the first and second loss functions prior to or during the respective iterative process to change an effect of the cut-off plane in the respective training.

In embodiments, the execution of the sequence of programmed instructions causes the computer processing system to train the at least one first neural network model to approximate the ROI based on an anatomical landmark.

In embodiments, each of the first and second neural network models is a deep neural network having more than two hidden layers.

It will be appreciated that the aspects of the disclosed subject matter can be implemented, fully or partially, in hardware, hardware programmed by software, software instruction stored on a computer readable medium (e.g., a non-transitory computer readable medium), or any combination of the above. For example, components of the disclosed subject matter, including components such as a controller, module, model, neural network, or any other feature, can include, but are not limited to, a personal computer or workstation or other such computing system that includes a processor (e.g., graphics processing unit), microprocessor, microcontroller device, or is comprised of control logic including integrated circuits such as, for example, an application specific integrated circuit (ASIC). Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of any process, method, or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of any process, method, or algorithm disclosed herein may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

It is thus apparent that there is provided, in accordance with the present disclosure, systems and methods for image cropping and anatomical structure segmentation in medical imaging. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method comprising:
   training at least one first neural network model using a first data set of medical images, each of the medical images in the first data set including a contour of an anatomical structure therein and at least one of a region-of-interest (ROI) around the anatomical structure and a cut-off plane with respect to the anatomical structure, each first neural network model being trained to approximate the ROI or the cut-off plane;
   based on data from the at least one first neural network model, cropping medical images of a second data set, each of the medical images in the second data set including a contour of the anatomical structure; and
   training at least one second neural network model using the cropped medical images, each second model being trained to approximate the contour of the anatomical structure.

2. The method of claim 1, wherein the medical images of the first and second data sets are the same.

3. The method of claim 1, further comprising:
   processing a third data set of medical images using the at least one first neural network model to generate cropping data;
   cropping the third data set of medical images based at least on the cropping data from the at least one first neural network model; and
   processing the cropped third data set of medical images using the at least one second neural network model to generate one or more contours of anatomical structures in the third data set of medical images.

4. The method of claim 3, wherein at least one of the generated contours has a substantially straight edge or substantially flat surface.

5. The method of claim 3, further comprising, after processing by the at least one second neural network model, processing the third data set of medical images using at least one algorithm that modifies the generated contours to have a substantially straight edge or substantially flat surface.

6. The method of claim 5, wherein the at least one algorithm comprises a heuristic algorithm.

7. The method of claim 3, further comprising developing a treatment plan for radiotherapy based at least on the third data set of medical images and the generated contours.

8. The method of claim 7, wherein the cropping the third data set of medical images is further based on an irradiation field placement of the radiotherapy.

9. The method of claim 1, wherein the training the at least one second neural network model also uses definitions of cut-off planes in the medical images of the second data set.

10. The method of claim 1, wherein the training of the at least one first neural network model is a process that iterates until a first loss function meets first predetermined criteria, the training of the at least one second neural network model is a process that iterates until a second loss function meets second predetermined criteria, and further comprising modifying one of the first and second loss functions to change an effect of the cut-off plane during the respective training.

11. The method of claim 1, wherein the at least one first neural network model is trained to approximate the ROI based on an anatomical landmark.

12. The method of claim 1, wherein the contour of the anatomical structure in the first data set or the second data set is custom defined by a user.

13. The method of claim 1, wherein each of the first and second neural network models is a deep neural network having more than two hidden layers.

14. The method of claim 1, wherein the anatomical structure in the first data set or the second data set comprises an organ to be irradiated or an organ-at-risk.

15. A system comprising:
one or more data storage devices storing at least one first neural network model and at least one second neural network model, each first neural network model having been trained to approximate a region-of-interest (ROI) around an anatomical structure or a cut-off plane with respect to the anatomical structure, each second neural network model having been trained to approximate a contour of the anatomical structure; and
one or more processors operatively coupled to the one or more data storage devices and configured to:
employ the at least one first neural network model to process one or more medical images of a patient to generate cropping data;
based at least one the cropping data from the at least one first neural network model, crop the one or more medical images of the patient; and
employ the at least one second neural network model to process the one or more cropped medical images of the patient to generate one or more contours of anatomical structures in the medical images of the patient.

16. The system of claim 15, wherein the one or more processors is further configured to:
train the at least one first neural network model to approximate ROIs or cut-off planes using a first data set of medical images, each of the medical images of the first data set including a contour of an anatomical structure therein and at least one of a ROI around the anatomical structure or a cut-off plane with respect to the anatomical structure;
based on data from the first neural network model, crop medical images of a second data set, each of the medical images of the second data set including a contour of anatomical structure therein; and
train the at least one second neural network model to approximate contours of anatomical structures using the cropped medical images of the second data set.

17. The system of claim 15, wherein at least one of the generated contours has a substantially straight edge or substantially flat surface.

18. The system of claim 15, further comprising:
a radiotherapy device configured to deliver radiation treatment to a patient,
wherein the one or more processors are further configured to control the radiotherapy device to irradiate the patient according to a treatment plan based at least on the one or more medical images of the patient and the generated contours.

19. The system of claim 15, wherein the one or more processors is further configured to, using at least one algorithm, process the one or more medical images of the patient to modify the generated contours to have a substantially straight edge or substantially flat surface.

20. The system of claim 19, wherein the at least one algorithm comprises a heuristic algorithm.

21. The system of claim 15, wherein the one or more processors is configured to crop the one or more medical images of the patient based on an irradiation field placement of a radiotherapy.

22. The system of claim 16, wherein the one or more processors is configured to train the at least one second neural network model using definitions of cut-off planes in the medical images of the second data set.

23. The system of claim 16, wherein the one or more processors is configured to:
train the at least one first neural network model by an iterative process and calculate a first loss function after each iteration;
train the at least one second neural network model by an iterative process and calculate a second loss function after each iteration; and
receive input to modify one of the first and second loss functions prior to or during the respective iterative process to change an effect of the cut-off plane in the respective training.

24. The system of claim 16, wherein the one or more processors is configured to train the at least one first neural network model to approximate the ROI based on an anatomical landmark.

25. The system of claim 15, wherein each of the first and second neural network models is a deep neural network having more than two hidden layers.

26. A non-transitory computer-readable storage medium upon which is embodied a sequence of programmed instructions, and a computer processing system that executes the sequence of programmed instructions embodied on the computer-readable storage medium to cause the computer processing system to:
process one or more medical images of a patient using at least one first neural network model to generate cropping data, each first neural network model having been trained to approximate a region-of-interest (ROI) around an anatomical structure or a cut-off plane with respect to the anatomical structure;

crop the one or more medical images of the patient based at least on the cropping data from the at least one first neural network model; and process the one or more cropped medical images of the patient using at least one second neural network model to generate one or more contours of anatomical structures in the one or more medical images of the patient, each second neural network model having been trained to approximate contours of anatomical structures.

27. The non-transitory computer-readable storage medium and computer processing system of claim 26, wherein the execution of the sequence of programmed instructions further causes the computer processing system to:

train the at least one first neural network model using a first data set of medical images, each of the medical images in the first data set including a contour of an anatomical structure therein and at least one of a region-of-interest (ROI) around the anatomical structure or a cutoff plane with respect to the anatomical structure;

based on data from the at least one first neural network model, crop medical images of a second data set, each of the medical images in the second data set including a contour of the anatomical structure; and train the at least one second neural network model using the cropped medical images.

28. The non-transitory computer-readable storage medium and computer processing system of claim 26, wherein at least one of the generated contours has a substantially straight edge or substantially flat surface.

29. The non-transitory computer-readable storage medium and computer processing system of claim 26, wherein the execution of the sequence of programmed instructions further causes the computer processing system to:

process the one or more medical images of the patient using at least one algorithm that modifies the generated contours to have a substantially straight edge or substantially flat surface.

30. The non-transitory computer-readable storage medium and computer processing system of claim 29, wherein the at least one algorithm comprises a heuristic algorithm.

31. The non-transitory computer-readable storage medium and computer processing system of claim 26, wherein the execution of the sequence of programmed instructions causes the computer processing system to crop the one or more medical images of the patient based on an irradiation field placement of a radiotherapy.

32. The non-transitory computer-readable storage medium and computer processing system of claim 27, wherein the execution of the sequence of programmed instructions causes the computer processing system to train the at least one second neural network model using definitions of cut-off planes in the medical images of the second data set.

33. The non-transitory computer-readable storage medium and computer processing system of claim 27, wherein the execution of the sequence of programmed instructions causes the computer processing system to:

train the at least one first neural network model by an iterative process and calculate a first loss function after each iteration;

train the at least one second neural network model by an iterative process and calculate a second loss function after each iteration; and receive input to modify one of the first and second loss functions prior to or during the respective iterative process to change an effect of the cut-off plane in the respective training.

34. The non-transitory computer-readable storage medium and computer processing system of claim 27, wherein the execution of the sequence of programmed instructions causes the computer processing system to train the at least one first neural network model to approximate the ROI based on an anatomical landmark.

35. The non-transitory computer-readable storage medium and computer processing system of claim 26, wherein each of the first and second neural network models is a deep neural network having more than two hidden layers.

* * * * *